United States Patent [19]

Schneider et al.

[11] 4,087,553
[45] May 2, 1978

[54] FUNGICIDAL 2,6-DINITRODIPHENYLTHIOETHERS

[75] Inventors: Louis Schneider, Elizabeth; David E. Graham, Westfield, both of N.J.

[73] Assignee: GAF Corporation, New York, N.Y.

[21] Appl. No.: 743,278

[22] Filed: Nov. 19, 1976

[51] Int. Cl.² .................. A01N 9/12; C07C 149/34
[52] U.S. Cl. .................... 424/337; 260/609 E
[58] Field of Search .................. 260/609 E; 424/337

[56] References Cited

U.S. PATENT DOCUMENTS

| | | | |
|---|---|---|---|
| 2,909,457 | 10/1959 | Birum | 424/337 |
| 3,322,525 | 5/1967 | Martin et al. | 260/609 E |
| 3,420,892 | 1/1969 | Martin et al. | 260/609 E |
| 3,542,880 | 11/1970 | Rohr et al. | 260/609 E |

FOREIGN PATENT DOCUMENTS 999,893  7/1965  United Kingdom ............... 424/337

OTHER PUBLICATIONS

C.A. 67:32406m, Gupta et al. (1967).

*Primary Examiner*—Joseph Paul Brust
*Assistant Examiner*—Molly C. Eakin
*Attorney, Agent, or Firm*—Walter C. Kehm; Walter Katz

[57] ABSTRACT

Fungicidal 2,6-dinitrodiphenylthioethers having the formula:

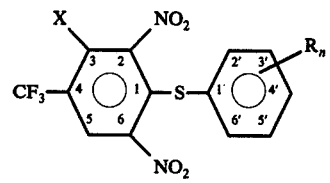

where X is halogen,
R is halogen or methyl substituted at the 2', 4' or 5' positions, $n$ is 0–3.

The compounds are particularly useful against bean rust and bean mildew.

10 Claims, No Drawings

FUNGICIDAL 2,6-DINITRODIPHENYLTHIOETHERS

BACKGROUND OF THE DISCLOSURE

1. Field of the Invention

This invention relates to a class of fungicides which are effective for many agricultural uses.

2. Description of the Prior Art

Diphenylthioether compounds are known in the art as being useful agricultural chemicals. Accordingly, it is the object of this invention to provide new diphenylthioethers, and particularly those which exhibit fungicidal activity.

SUMMARY OF THE INVENTION

The present invention provides fungicidal 2,6-dinitrodiphenylthioethers having the formula:

[Structure showing CF₃ and X substituted benzene ring with two NO₂ groups, connected via S to a second phenyl ring with R_n substituent]

where X is halogen,
R is halogen or methyl substituted at the 2', 4' or 5' positions, and n is 0–3.

The compounds are particularly useful as fungicides against bean rust, and bean mildew.

DESCRIPTION OF THE PREFERRED EMBODIMENTS

The compounds of this invention are prepared by condensing a phenyl halide with a thiophenol to produce the desired diphenylthioether, as follows:

[Reaction scheme: Compound (I) with X, CF₃, Hal, and two NO₂ groups + HS-phenyl-R_n (II) → Compound (III) diphenylthioether]

where Hal is a halogen.

The presence of the two nitro groups adjacent the halogen substituent on starting material I activates that position on the ring so condensation with the thiophenyl, reactant II, can take place at the desired position of the benzene ring only. The reaction proceeds by nucleophilic displacement of the halogen atom by the thiophenoxy group to produce the desired diphenylthioether III.

Intermediate I is produced by dinitration of the corresponding dihalo compound IV:

[Structure IV: benzene with X, CF₃, and Hal substituents]

Nitration is conducted in a mixture of nitric acid to produce the dinitrated compound, as described in U.S. Pat. No. 3,586,725. Precursor IV is commercially available from the Hooker Chemical Company, Buffalo, N.Y. The thiophenyl reactants used herein also are commercially available starting materials.

Generally the reaction is carried out by stirring the reactants in a basic medium for an extended period of time at cooling temperatures in a suitable solvent, such as acetone. The dilute alkali serves as an acceptor for the hydrogenhalide which is released during the reaction.

Suitable alkaline compounds useful for this reaction include an alkali metal hydroxide or carbonate, such as sodium hydroxide, sodium carbonate, potassium carbonate, and the like. Upon completion of the reaction, the alkali halide is filtered off and the acetone is removed by roto-evaporation. The remaining product then is recrystallized from methanol.

The compounds of the invention are useful as agricultural fungicides when applied to the soil at the rate of about 1 to 25 lbs. per acre or as a foliar spray at concentrations of about 31 to 260 ppm. They show foliar fungicidal activity against the following pathogens: bean rust and bean mildew which cause severe economic losses in bean crops.

The materials of the present invention may be applied to those fungus susceptible plants on site at a rate of about 1 or less to about 25 pounds per acre depending on various circumstances of the susceptibility to the fungus, the weather, the stage of growth and various other factors. The material may be applied as a dust or spray. As a dust it is more practical to extend it with diluents such as bentonite, chalk, clay, diatomaceous earth, fullers earth, mica, ground slate or any of the other usual carriers for agricultural chemicals. As a spray it may be incorporated into water as a solution. The higher molecular weight compounds may be dissolved first in a solvent, such as an alcohol, or a petroleum fraction, such as isoparaffinic hydrocarbons, naphtha or kerosene, which may act either as a cosolvent or which may be emulsified in water. For low-volume applications the material may be dissolved in a suitable solvent and fogged or sprayed without water. Usually it is desirable to incorporate emulsifying agents and other wetting agents to insure complete contact with the fungus.

Following are examples of preparation of the compounds of the invention, and are presented by way of illustration and are not intended to be limiting unless otherwise specified.

EXAMPLE 1

·3-Chloro-4-Trifluoromethyl-2,6-Dinitrodiphenylthioether 1,3-Dichloro-2,6-dinitro-4-trifluoromethylbenzene (30.5 g., 0.1 mole), potassium carbonate (20.29, 0.15 mole), and acetone (100 ml.) were charged into 250 cc 4-neck flask equipped with a stirrer, condenser, thermometer and a drying tube. Thiophenol (11.1 g., 0.1 mole) was added at 0° C., and the mixture was stirred at 0°–5° C. for one hour. Potassium chloride was filtered off and the acetone removed by rotoevaporation. The residue was crystallized from four parts of methanol yielding 15 g. of product, m.p. 93°–95° C.

Anal. Calcd. for $C_{13}H_6F_3ClN_2O_4S$: N, 7.13; Cl, 9.02; S, 8.47; Found: N, 6.87; Cl, 8.85, S, 8.75.

EXAMPLE 2

3-Chloro-4-Trifluoromethyl-2,6-Dinitro-4'-Methyldiphenylthioether 1,3-Dichloro-2,6-dinitro-4-trifluoromethylbenzene (30.5 g., 0.1 mole), p-thiocresol (12.4 g., 0.1 mole) potassium carbonate (20.2 g., 0.15 mole), and acetone (100 ml.) were reacted and worked up as in Example 1 to yield 43 g. of crude product, which was recrystallized from methanol m.p. 94°–95° C.

Anal. Calcd. for $C_{14}H_8F_3ClN_2O_4S$: N, 7.13; Cl, 9.02; S, 8.16; Found: N, 6.88; Cl, 8.72; S, 7.80.

EXAMPLE 3

3-Chloro-4-Trifluoromethyl-2,6-Dinitro-4'-Chlorodiphenylthioether 1,3-Dichloro-2,6-dinitro-4-trifluoromethylbenzene (30.5 g., 0.1 mole), p-chlorothiophenol (14.5 g., 0.1 mole), potassium carbonate (20.2 g., 0.15 mole), and acetone (100 ml.) were reacted and worked up as in Example 1 to yield the crude product which was recrystallized from methanol.

EXAMPLE 4

3-Chloro-4-Trifluoromethyl-2,6-Dinitro-2',4'-Dichlorodiphenylthioether 1,3-Dichloro-2,6-dinitro-trifluoromethylbenzene (30.5 g., 0.1 mole), 2,4-dichlorothiophenol (17.9 g., 0.1 mole) potassium carbonate (13.8 g., 0.1 mole) and acetone (100 ml.) were reacted and worked up as in Example 1 to yield the crude product which was recrystallized from methanol.

EXAMPLE 5

3-Chloro-4-Trifluoromethyl-2,6-Dinitro-2',4',5-Trichlorodiphenylthioether 1,3-Dichloro-2,6-dinitro-4-trifluoromethylbenzene (30.5 g., 0.1 mole), 2,4,5-trichlorothiophenol (21.4 g., 0.1 mole) and acetone (100 ml.) were reacted and worked up as in Example 1 to yield the crude product, which was recrystallized from methanol.

EXAMPLE 6

FOLIAGE FUNGICIDE TESTS

The products of Examples 1 and 2 were tested on bean rust as follows: Pinto beans grown in 2.5 inch pots for 9 to 12 days are sprayed while plants are rotating on a turntable with 100 ml. of a formulation at 125, 63 and 31 ppm. After the spray deposit dries, plants are placed in a moist chamber at 70° F. for 24 hours. After 7 to 9 days the severity of pustule formation is rated on a scale of 0 (no reduction) to 10 (complete elimination of infection) and compared with the commercial standard Plantvax, 2,3-dihydro-5-carbanilido-6-methyl-1,4-oxathiin-4,4-dioxide.

| | Fungitoxicity Ratings | | |
|---|---|---|---|
| Conc., ppm | Compound of Ex. 1 | Ex. 2 | Plantvax |
| 125 | 7.5 | 9.0 | 10 |
| 62 | 9.0 | 8.0 | 10 |
| 31 | 8.0 | — | 10 |

EXAMPLE 7

The products of Examples 1 and 2 were tested on bean powdery mildew as follows: Healthy young bean plants with fully expanded primary leaves in 2½ inch pots were placed for 2 days on a greenhouse bench between two rows of infected plants covered with a mass of white, powdery conidia, so that they were exposed to a shower of conidia.

The primary test plants with incipient infection were atomized while rotating on a turntable with a suspension of 125, 62 and 31 ppm of a test material. The treated plants were then returned to the greenhouse bench near infected plants. After 7 days preliminary observations were made on the eradication of established infection present on the primary leaves at the time of spraying. The plants were reexamined 7 days later for infection on new growth as well as on the primary leaves to determine residual and systemic effects on the fungus. On both dates the leaves were rated on a scale of 0 (no suppression) to 10 (complete eradication or prevention of infection), and compared to the commercial standard Karathane, 2,4-dinitro-6-octylphenylcrotonate.

| | Fungitoxicity Rating | | |
|---|---|---|---|
| Conc., ppm. | Compound of Ex. 1 | Ex. 2 | Karathane |
| 125 | 5.5 | 9.5 | 10 |
| 62 | 8.0 | 9.5 | 10 |
| 31 | 3.0 | 6.0 | 10 |

What is claimed is:

1. 3-Chloro-4-trifluoromethyl-2,6-dinitrodiphenylthioether.

2. 3-Chloro-4-trifluoromethyl-2,6-dinitro-4'-methyldiphenylthioether.

3. 3-Chloro-4-trifluoromethyl-2,6-dinitro-4'-chlorodiphenylthioether.

4. 3-Chloro-4-trifluoromethyl-2,6-dinitro-2',4'-dichlorodiphenylthioether.

5. 3-Chloro-4-trifluoromethyl-2,6-dinitro-2',4',5'-trichlorodiphenylthioether.

6. A method of controlling undesired fungi comprising applying thereto a fungicidally effective amount of a compound of claim 1.

7. A method of controlling undesired fungi comprising applying thereto a fungicidally effective amount of a compound of claim 2.

8. A method of controlling undesired fungi comprising applying thereto a fungicidally effective amount of a compound of claim 3.

9. A method of controlling undesired fungi comprising applying thereto a fungicidally effective amount of a compound of claim 4.

10. A method of controlling undesired fungi comprising applying thereto a fungicidally effective amount of a compound of claim 5.

* * * * *